(12) United States Patent
Strocchia-Rivera

(10) Patent No.: US 7,508,511 B2
(45) Date of Patent: *Mar. 24, 2009

(54) METHOD AND APPARATUS FOR IMPROVED ELLIPSOMETRIC MEASUREMENT OF ULTRATHIN FILMS

(75) Inventor: Carlos Strocchia-Rivera, Highland, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/127,240

(22) Filed: May 27, 2008

(65) Prior Publication Data
US 2008/0259333 A1 Oct. 23, 2008

Related U.S. Application Data

(63) Continuation of application No. 11/688,366, filed on Mar. 20, 2007, now Pat. No. 7,394,539, which is a continuation of application No. 10/904,462, filed on Nov. 11, 2004, now Pat. No. 7,280,209.

(51) Int. Cl.
G01J 4/00 (2006.01)

(52) U.S. Cl. .................................................. 356/369
(58) Field of Classification Search ................. 356/369, 356/364; 250/559.09, 225
See application file for complete search history.

(56) References Cited

U.S. PATENT DOCUMENTS

| 4,873,430 A * | 10/1989 | Juliana et al. ............... 250/225 |
| 2002/0180091 A1 | 12/2002 | Norley et al. |
| 2002/0180991 A1 * | 12/2002 | Takoudis et al. ............ 356/630 |
| 2003/0227623 A1 | 12/2003 | Zhan et al. |
| 2004/0085544 A1 | 5/2004 | De Groot |

* cited by examiner

Primary Examiner—Roy M Punnoose
(74) Attorney, Agent, or Firm—Cantor Colburn LLP; Lisa Jaklitsch

(57) ABSTRACT

A method for implementing ellipsometry for an ultrathin film includes directing a polarized light beam incident upon a sample surface, receiving an initial reflected beam from the sample surface and redirecting the initial reflected beam back upon said sample surface one or more times so as to produce a final reflected beam. The final reflected beam is received through an analyzer and at a detector so as to determine characteristics of the ultrathin film.

8 Claims, 3 Drawing Sheets

METHOD AND APPARATUS FOR IMPROVED ELLIPSOMETRIC MEASUREMENT OF ULTRATHIN FILMS

CROSS REFERENCE TO RELATED APPLICATION

This application is a continuation application of U.S. Ser. No. 11/688,366, filed Mar. 20, 2007 now U.S. Pat. No. 7,394,539, which is a continuation application of U.S. Ser. No. 10/904,462, filed Nov. 11, 2004 now U.S. Pat. No. 7,280,209, the disclosures of which are incorporated by reference herein in their entirety.

BACKGROUND

The present invention relates generally to semiconductor device manufacturing, and, more particularly, to a method and apparatus for improved ellipsometric measurement of ultrathin films.

Ellipsometry is an optical technique that uses polarized light to probe the properties of a sample. One of the most common applications of ellipsometry is the analysis of thin films. Through the analysis of the state of polarization of the light that interacts with a sample, ellipsometry can yield certain information about the properties of such films. For example, depending on what is already known about the sample, the technique can probe a range of properties including the layer thickness, index of refraction, morphology, or chemical composition.

Generally, optical ellipsometry may be defined as the measurement of the state of polarized light waves. An ellipsometer measures the changes in the polarization state of light when it interacts with a sample. The most common ellipsometer configuration is a reflection ellipsometer, although transmission ellipsometers are also sometimes used. If linearly polarized light of a known orientation is reflected or transmitted at oblique incidence from a sample surface, then the resultant light becomes elliptically polarized. The shape and orientation of the ellipse depends on the angle of incidence, the direction of the polarization of the incident light, the wavelength of the incident light, and the Fresnel properties of the surface.

The polarization of the light is measured for use in determining certain characteristics of the sample. For example, in one conventional null ellipsometer, the polarization of the reflected light may be measured with a quarter-wave plate, followed by an analyzer. The orientation of the quarter-wave plate and the analyzer are varied until no light passes though the analyzer (i.e., a null is attained). Based on these orientations and the direction of polarization of the incident light, a description of the state of polarization of the light reflected from the surface may be calculated and the sample properties deduced.

Two characteristics of ellipsometry make its use particularly attractive in the field of semiconductor manufacturing. First, since ellipsometry is a nondestructive technique, it is suitable for in situ observation of a sample. Second, the technique is extremely sensitive in that small changes of a film may, in certain instances, be measured down to a sub-monolayer of atoms or molecules. Accordingly, ellipsometry has been widely used in areas such as physics, chemistry, materials science, biology, metallurgical engineering and biomedical engineering, to name a few. At the same time, however, advances in microelectronics fabrication are rapidly surpassing current capabilities in metrology. In order to enable the continued scaling of future generations of microelectronics, advances in specific metrology capabilities must also follow suit, such as the ability to measure the properties of ultra-thin films (e.g., thicknesses on the order of 20 angstroms or less) over sub-micron lateral dimensions.

Unfortunately, existing ellipsometry systems have difficulty in measuring and distinguishing between certain characteristics (e.g., index of refraction, thickness, etc.) of ultrathin films having varying optical properties. In the past, certain optical properties (such as material composition) have been assumed for thin films such as gate dielectrics where the dielectric material utilized was an oxide or nitride material, for example. However, with the use of more advanced ultrathin gate dielectrics, the traditional assumptions as to the composition of the dielectric material are no longer reliable for use in ellipsometric measurements. In particular, these ultrathin films do not produce enough of a phase shift on an incident beam to adequately distinguish between film thickness and film composition. Thus, a need exists for improving conventional ellipsometric techniques so as to be able to reliably obtain the desired measurements of advanced ultrathin films.

SUMMARY

The foregoing discussed drawbacks and deficiencies of the prior art are overcome or alleviated by a method for implementing ellipsometry for an ultrathin film. In an exemplary embodiment, the method includes directing a polarized light beam incident upon a sample surface, receiving an initial reflected beam from the sample surface and redirecting the initial reflected beam back upon said sample surface one or more times so as to produce a final reflected beam. The final reflected beam is received through an analyzer and at a detector so as to determine characteristics of the ultrathin film.

In another embodiment, a method for determining film thickness and composition for an ultrathin film formed on a semiconductor substrate includes directing a polarized light beam incident upon a surface of the ultrathin film and receiving an initial reflected beam from said ultrathin film surface. The initial reflected beam has a phase shift with respect to the beam incident upon the ultrathin film surface. The initial reflected beam is redirected back upon the sample surface for a plurality of iterations, wherein the phase shift is increased with each of the iterations, so as to produce a final reflected beam. The final reflected beam is received through an analyzer and at a detector so as to determine the film thickness and composition of the ultrathin film.

In still another embodiment, an ellipsometry apparatus for determining characteristics of an ultrathin film includes a light source and a polarizer configured to direct a polarized light beam incident upon a sample surface. The apparatus further includes a means for receiving an initial reflected beam from the sample surface and redirecting the initial reflected beam back upon the sample surface one or more times so as to produce a final reflected beam. An analyzer is configured to receive the final reflected beam therethrough, and a detector is configured to determine characteristics of the ultrathin film.

BRIEF DESCRIPTION OF THE DRAWINGS

Referring to the exemplary drawings wherein like elements are numbered alike in the several Figures.

DETAILED DESCRIPTION

Disclosed herein is an improved method and apparatus for ellipsometry that will aid in the measurement and characterization of ultrathin films, such as those used in advanced semiconductor manufacturing. Briefly stated, the invention embodiments overcome the disadvantage of having minimal phase shift information by repeatedly directing the initially reflected beam back onto the sample so as to cumulatively increase the phase shift effect created by the ultrathin film. In so doing, the accumulated phase shift information of the repeatedly reflected beam provides increased reliability of the accuracy of the measured parameters of interest. It will be appreciated that the embodiments described hereinafter are not only applicable to the field of semiconductor manufacturing, but are also applicable to other areas where ultrathin films are measured and analyzed.

Figure 1:
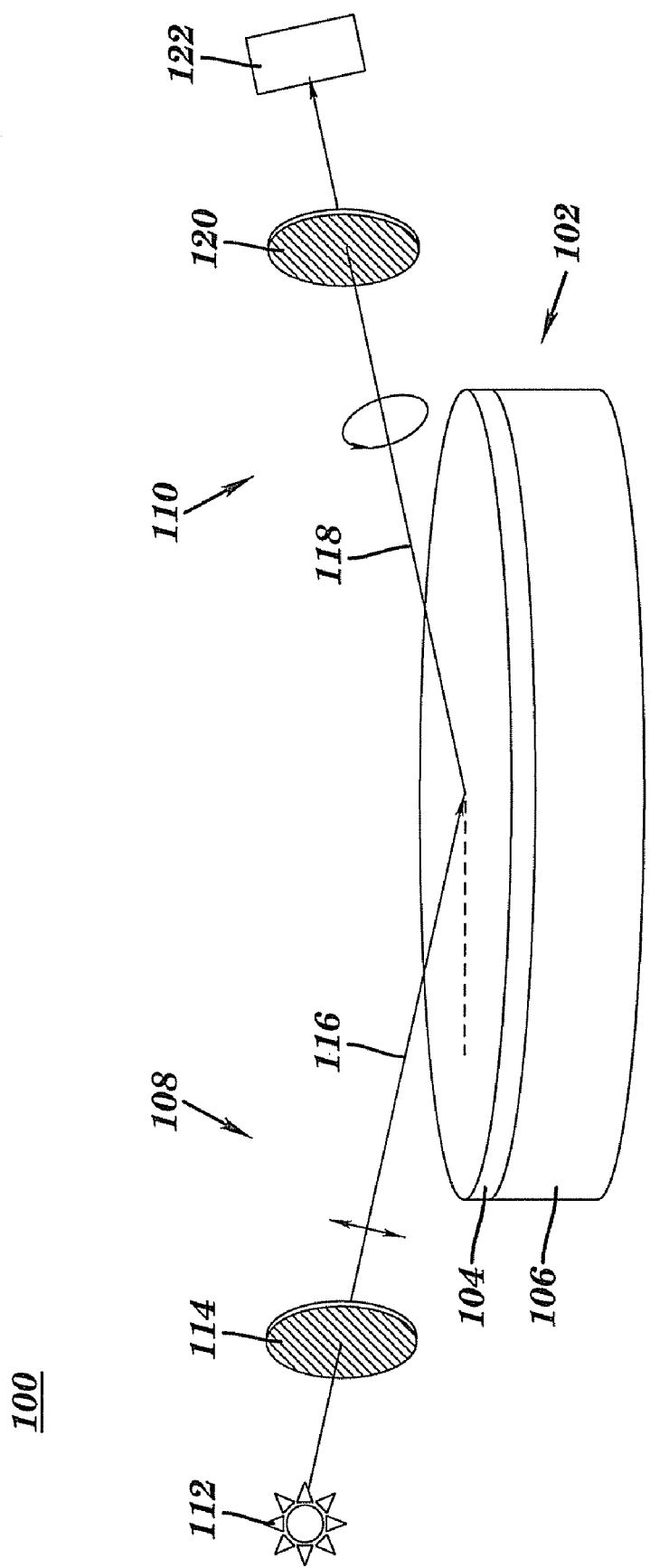
FIG. 1 is a schematic diagram of an existing reflection ellipsometer apparatus.

Referring initially to FIG. 1, there is shown a schematic diagram of an existing reflection ellipsometer apparatus 100 for performing ellipsometric measurements on a sample 102, in which an ultrathin layer 104 is formed upon a substrate 106. As is shown, the apparatus 100 includes a polarizer portion 108 and an analyzer portion 110. The polarizer portion 108 includes a light source 112 such as a laser (e.g., a 632.8 nm helium/neon laser or a 650-850 nm semiconductor diode laser) and a polarizer 114, which provides a state of polarization for an incident light beam 116 at a non-normal angle with respect to the surface of the sample 110 (e.g., about 20° with respect to the sample surface plane, or about 70° with respect to the normal of the surface plane). The incident light beam 116 is typically linearly polarized (as is depicted in FIG. 1) with finite field components $E_p$ and $E_s$ in the directions parallel and perpendicular to the surface plane. (However, in other systems, the incident beam 116 may also be elliptically polarized light or circularly polarized light.)

Upon reflection of the incident light beam 116 off the ultrathin layer 104 of the sample 102, the initial linear polarization of the reflected light beam 118 is changed to a slight elliptical polarization due to the properties of the ultrathin layer 114, in accordance with the Fresnel equations. The reflected light beam 118 is then analyzed with the analyzer portion 110 of the ellipsometer apparatus 100. In particular, the analyzer portion 110 includes an analyzer 120 (e.g., a second polarizer generally crossed with the first polarizer 114) and a detector 122.

In order to measure the polarization of the reflected light beam, the operator may change the angle of the polarizer 114, the analyzer 120, and/or other additional optical components until a minimal signal is detected. For example, the minimum signal is detected if the light 118 reflected by the sample 102 is linearly polarized, while the analyzer 120 is set so that only light with a polarization that is perpendicular to the incoming polarization is allowed to pass. The angle of the analyzer 120 is therefore related to the direction of polarization of the reflected light 118 if the minimum condition is satisfied. The apparatus is "tuned" to this null condition (e.g., generally automatically under computer control), and the positions of the polarizer 114, the analyzer 120, and the incident angle of the light 116 relative to the plane of the sample surface are used to calculate the fundamental quantities of ellipsometry; i.e., the so called (psi ($\Psi$), delta ($\Delta$)) pair, given by the expression:

$$\frac{r_p}{r_s} \tan\Psi(e^{j\Delta})$$

where $r_p$ and $r_s$ are the complex Fresnel reflection coefficients for the transverse magnetic and transverse electrical waves of the polarized light, respectively. Thus, from the ellipsometry pair ($\Psi$, $\Delta$), the thickness and index of refraction of a thin film may be determined. It will also be recognized that various other ways of analyzing the reflected light are also possible. For example, one possible alternative would be to vary the angle of the analyzer 120 to collect polarization information.

Figure 2:
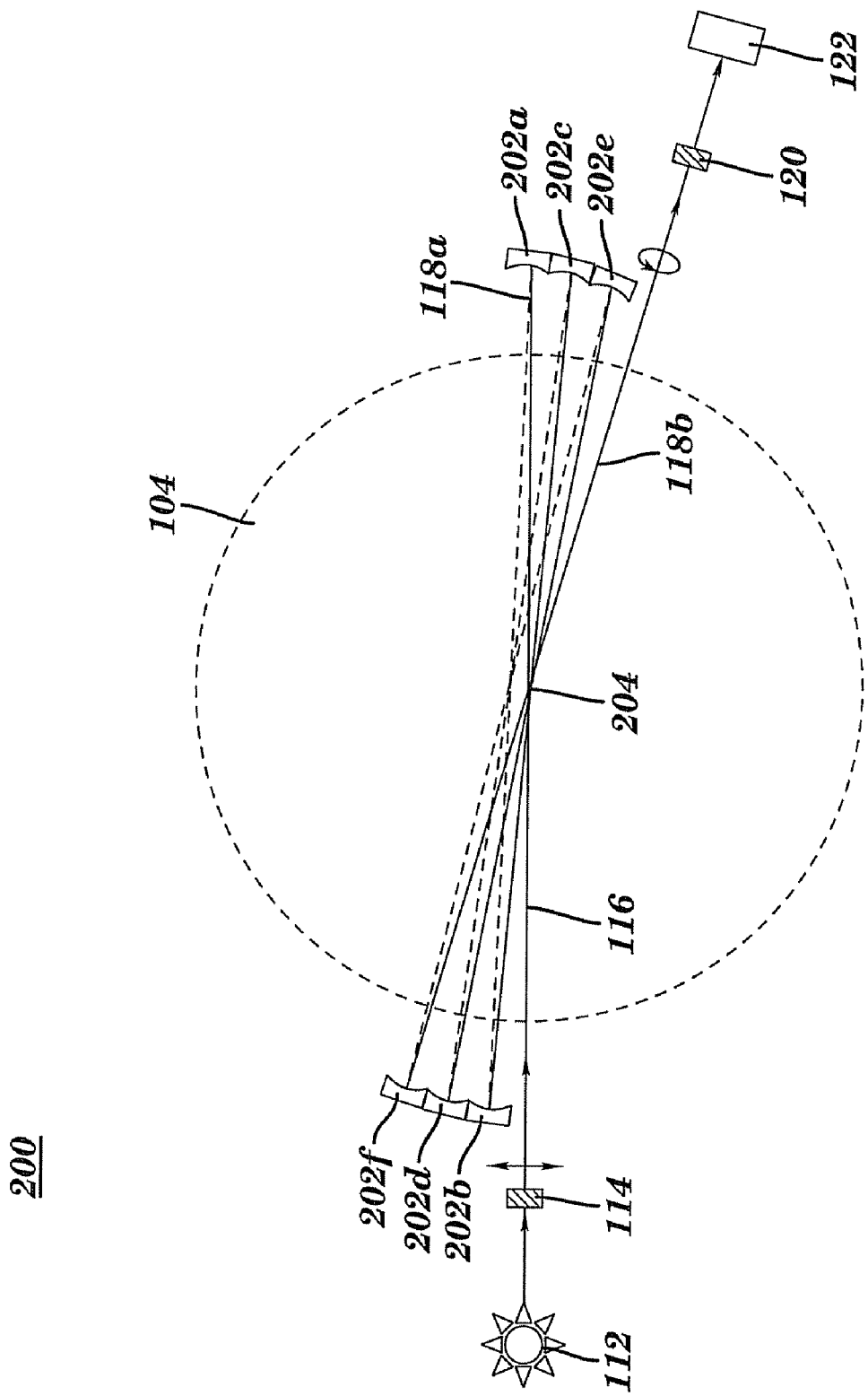
FIG. 2 is a schematic diagram of an ellipsometer apparatus specifically configured to repeatedly direct the initially reflected light back upon an ultrathin film surface, in accordance with an embodiment of the invention.

As mentioned previously, however, ultra-thin films impart very little phase shift with respect to the incident light beam. Because the measured film characteristics (thickness and optical properties) are based on the extent of the phase shift imparted by the ultrathin film 104, the ellipsometer apparatus 100 of FIG. 1 is not suited for reliable characterization thereof due to this minimal phase shift. Therefore, in accordance with an embodiment of the invention, FIG. 2 illustrates an ellipsometer apparatus 200 specifically configured to repeatedly direct the initially reflected light back upon the ultrathin film surface using reflective devices that maintain the phase shift of the initially reflected light. In this manner, the multiple passes will cumulatively increase the phase shift such that it can be more confidently measured. Moreover, the angle of incidence and orientation variations may be introduced, which will provide additional information not normally available with a classic ellipsometer or spectroscopic ellipsometer.

More specifically, the ellipsometer apparatus 200 includes a plurality of reflective devices 202a-202f (e.g., mirrors having a minimum or a fixed/known phase shift) configured within the optical path prior to the analyzer 120. A first mirror 202a receives the initial reflected beam 118a, redirecting it to a second mirror 202b in a non-interacting manner (indicated by a dashed line) with respect to the film 104 at a point near the origin of the incident light beam 116. The second mirror 202b then redirects the light back off of the film 104, at approximately the same point 204 as the incident light beam 116. This redirected reflection process is then repeated using subsequent pairs of mirrors (e.g., 202c/202d, 202e/202f) until a suitable amount of iterations of phase shifting of the beam is achieved.

It should be appreciated that the schematic depiction of FIG. 2 is not to scale, and that the spacing, arrangement, and particular number of the mirrors 202a-202e are shown for illustrative purposes only. It will further be understood that in the plan view of FIG. 2, the mirrors 202a-202e are situated above the plane of the film 104 and that the reflected beams are incident upon the film 104 at about the location of the point 204 of reflection. In the embodiment illustrated, the individual mirrors are oriented such that the redirected incident beams are incident at the original point 204 of reflection. The surfaces of mirrors 202a-202e may be further be curved in a manner such that the reflected beams are refocused to the initial point 204 of reflection.

It will also be appreciated that, in addition to using an individual mirror for each of the reflections, a single mirror on opposite sides of the sample could also be used, provided the mirror geometry is appropriately configured. (In other words, individual mirrors 202a, 202c and 202e could be functionally implemented as a first mirror on one side of the wafer 104, while mirrors 202b, 202d and 202f could be functionally implemented as a second mirror on the opposite side of the wafer 104.) In any case, a final reflected beam 118b (after all iterations) is directed to the analyzer 120 and detector 122 for measurement of the ellipsometric parameters. Again, the mirrors 202a-202e are configured such that the polarization of the final reflected beam 118b is substantially the same is the polarization of the reflected beam 118a, only with the effect of the phase shift being accumulated such that it is more easily measured.

The specific number of mirrors or, more generally, the number of reflections may be adjusted (i.e., automatically inserted or removed where needed) such that the amount of the phase shift is controllable for maximum confidence in the measurement process. In addition, the mirrors may also be removed entirely in order to return to a classical ellipsometer configuration. Still another advantage of the embodiment of FIG. 2 stems from the fact that the angle of incidence that each mirror introduces in reflecting the light back off the sample may be varied such that additional information (e.g., ellipsometric parameters as a function of angle of incidence) can be obtained.

Depending upon the specific application, measurement and film composition involved, an appropriate number of reflective passes may be implemented. For example, with currently manufactured gate oxides, a total of 10 passes (reflections) may be suitable for accurate film thickness and composition determination. On the other hand, for a simple pass/fail test, a fewer number of reflections may be appropriate.

Figure 3:
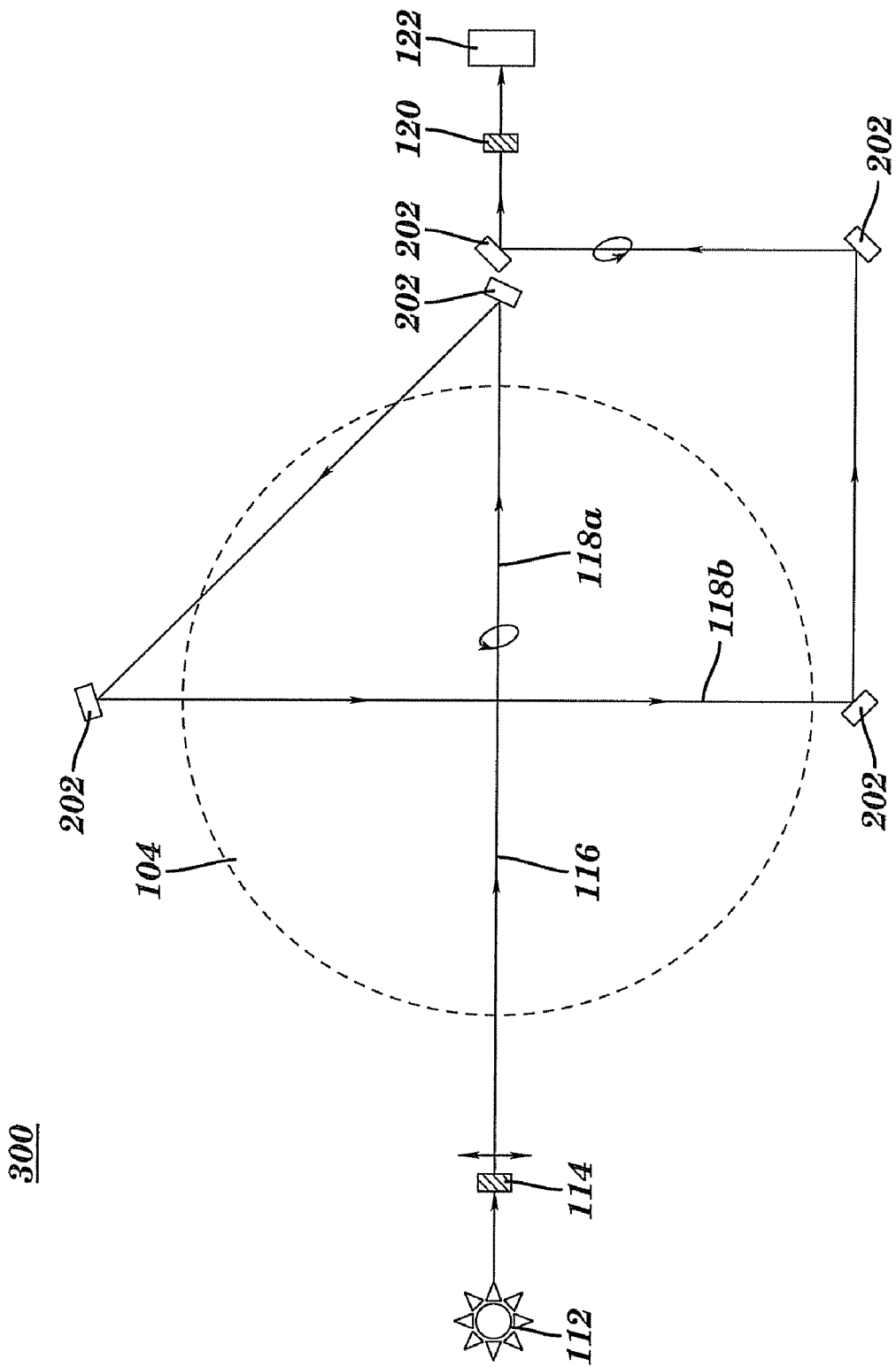
FIG. 3 is a schematic diagram of an alternative embodiment of the ellipsometer apparatus of FIG. 2.

Finally, FIG. 3 illustrates an alternative embodiment of an ellipsometer apparatus 300, in which the path of the reflected beam is adjustably rerouted so that it does not follow the same direction as the original path. This approach may be useful, for example, for measuring material optical properties such as birefringence. As is shown in the exemplary embodiment of FIG. 3, the path of the initial reflected beam 118a is changed from an x-direction to a y-direction (orthogonal) for the final reflected beam 118b through the placement of various mirrors 202. It will be appreciated, however, that other directions across the sample may be realized, for several iterations where desired.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining film thickness and composition for an ultrathin film formed on a semiconductor substrate, the method comprising:
    directing a polarized light beam incident upon a surface of the ultrathin film;
    receiving an initial reflected beam from said ultrathin film surface, said initial reflected beam having a phase shift with respect to said beam incident upon the ultrathin film surface;
    redirecting said initial reflected beam back upon said sample surface for a plurality of iterations, wherein said phase shift is increased with each of said iterations, so as to produce a final reflected beam; and
    receiving said final reflected beam through an analyzer and at a detector so as to determine the film thickness and composition of the ultrathin film.

2. The method of claim 1, wherein said redirecting said initial reflected beam back upon said ultrathin film surface is implemented through one or more reflective surfaces.

3. The method of claim 2, wherein said one or more reflective surfaces comprise individual mirrors.

4. The method of claim 2, wherein said one or more reflective surfaces comprise a first mirror on one side of said sample surface and a second mirror on an opposite side of said sample surface.

5. The method of claim 3, wherein said mirrors comprise curved surfaces configured for said redirecting said initial reflected beam back upon said ultrathin film surface.

6. The method of claim 1, further comprising redirecting said initial reflected beam back upon said ultrathin film surface along a substantially constant direction.

7. The method of claim 1, wherein said redirecting said initial reflected beam back upon said ultrathin film surface is implemented at least once in an orthogonal direction with respect to the direction of said initial reflected beam so as to measure birefringence of the ultrathin film.

8. The method of claim 3, wherein said individual mirrors are adjustable with respect to the positioning thereof.

* * * * *